(12) United States Patent
Adams

(10) Patent No.: US 6,349,233 B1
(45) Date of Patent: *Feb. 19, 2002

(54) NEURO-STIMULATION TO CONTROL PAIN DURING CARDIOVERSION DEFIBRILLATION

(75) Inventor: Theodore P. Adams, Edina, MN (US)

(73) Assignee: Angeion Corporation, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/121,161

(22) Filed: Jul. 23, 1998

Related U.S. Application Data

(63) Continuation of application No. 08/480,938, filed on Oct. 5, 1995, now Pat. No. 5,792,187, which is a continuation of application No. 08/020,635, filed on Feb. 22, 1993, now abandoned.

(51) Int. Cl.⁷ .............................. A61N 1/39; A61N 1/34
(52) U.S. Cl. ................. 607/5; 607/46; 607/63
(58) Field of Search ........................... 607/2, 5, 46, 47, 607/63, 4; 600/9, 13–15, 26

(56) References Cited

U.S. PATENT DOCUMENTS

| | | |
|---|---|---|
| 4,360,026 A | 11/1982 | Venin et al. |
| 4,550,733 A | 11/1985 | Liss et al. |
| 4,782,837 A | 11/1988 | Hogan |
| 4,924,880 A | 5/1990 | O'Neill et al. |
| 5,199,428 A | 4/1993 | Obel et al. |
| 5,203,326 A | 4/1993 | Collins |
| 5,215,086 A | 6/1993 | Terry, Jr. et al. |
| 5,330,515 A | 7/1994 | Rutecki et al. |

FOREIGN PATENT DOCUMENTS

| | | |
|---|---|---|
| WO | PCT/US91/08665 | 11/1991 |
| WO | WO 93/01861 | 2/1993 |

*Primary Examiner*—Kennedy J. Schaetzle
(74) *Attorney, Agent, or Firm*—Patterson, Thuente, Skaar & Christensen, P.A.

(57) ABSTRACT

A system and method for reducing the perceived pain by a patient occurring during cardioversion/defibrillation countershocks to the heart. The system comprises an electrode subsystem for positioning at least one electrode in contact with a patient, a pain reducing stimulation subsystem for providing pain reducing electromagnetic stimulation to the electrode subsystem, a cardioversion/defibrillation countershock subsystem so that delivery of pain reducing stimulation to the patient begins prior to a cardioversion/defibrillation countershock.

8 Claims, 5 Drawing Sheets

NEURO-STIMULATION TO CONTROL PAIN DURING CARDIOVERSION DEFIBRILLATION

This is a continuation of application No. 08/480,938 filed Oct. 5, 1995, now U.S. Pat. No. 5,792,187 which in turn is a continuation of application No. 08/020,635, filed on Feb. 2, 1993 now abandoned.

FIELD OF THE INVENTION

The present invention relates generally to pain reduction systems and more particularly to pain reduction utilizing electromagnetic electrodes proximate the cerebral cortex, vagus nerve and thoracic dorsal root nerves.

BACKGROUND OF THE INVENTION

Seldom are any surgical or therapeutic procedures performed without the perception of pain on the part of the patient. The medical specialty of anesthesiology has been developed to a high degree of sophistication for the relief and control of pain during surgery. Most application for pain relief use various chemical moieties delivered over numerous routes and modalities.

There are less conventional means of pain relief known comprising such entities as transcutaneous electrical nerve stimulators (TENS). These TENS units have received application retrospectively for local pain relief following surgical procedures.

The perception of pain is the end result of a process that began with stimulation of a peripheral sensory nerve and culminating in the conscious awareness of the pain at the cerebral cortex. Within the central nervous system there are several levels of organization at which the perception of pain may be interrupted. Perception begins with stimulation of a distal peripheral sensory nerve. The stimulation signal travels to the next level of sensory collection which is at the dorsal sensory nerve root ganglion just lateral to the spinal cord. The path then enters the spinal cord to the sensory tracts and ascends the spinal cord to the brain stem. Form the brain stem the sensory tracts then traverse to and innervate the thalami in the midbrain area. From the thalami the sensory stimulations are projected onto the cerebral cortex along the sensory strip. Each area of the cortex in this strip represents a surface area of the body in a fashion known as the homunculus distribution of the cerebral cortex.

Various procedures have been employed in the past to interrupt the perception of pain at these various levels, Peripheral nerve blockade is achieved through various methods, the more notable and commonplace are local nerve blocks with use of chemicals such as lidocaine injected at the procedure site. Dorsal root sensory ganglion blockade is achieved through spinal anesthesia by placing a chemical anesthetic agent such as lidocaine or one of its congeners within the spinal canal. Suitable narcotics, such a morphine, are also available for use within the spinal canal. The higher levels of sensory perception are interrupted through the modality known as general anesthesia. Such a method renders the patient unconscious during the period of general anesthesia.

It is in the area of local peripheral sensory nerve blockade that TENS units exercise their effect. Such units are applied in the area of the surgical wound after the procedure and set to deliver an electrical stimulus locally to the peripheral nerve endings. Similar TENS units have been utilized somewhat more proximal along the length of the peripheral nerve by applying the TENS unit to the ski of the back over the mid line area in an attempt to provide electrical stimulation to the dorsal spinal nerves as they exit the spinal column.

Chemical anesthetics used in local, regional and general anesthesia have numerous characteristics. A number of chemicals are available for local tissue injection providing direct anesthetic block at the sensory nerve ends. Other chemicals are for intravenous delivery and disseminate throughout the entire body to produce a general anesthesia effect. Intermediate to this, chemicals have been developed for direct injection into nerve bundles providing a regional type of anesthetic block, Such examples of regional anesthesia are axillary nerve blocks putting the arm to sleep, sacral nerve blocks putting the back of the leg to sleep, saddle blocks or epidural blocks that render the entire lower half of the body anesthetized.

Besides liquid injectable anesthetic agents, numerous gases are available for inhalation use in general anesthesia. Few of the gases are designed specifically for only pain relief. Instead, virtually all of these gases have been designed to render the patient unconscious as the main method of providing pain control. A notable exception is nitrous oxide when used during dental procedures. Nitrous oxide acts as an anxiolytic, altering the patient's apprehension of pain but not completely removing or ablating the perception of pain.

The liquid and gas chemicals all share numerous complications. All of these agents must be introduced within the patient's body where they undergo their primary purpose but must then be eliminated by the body. Each patient is different in their physiologic reaction to a chemical in terms of depth of anesthetic effect, elimination, duration of anesthetic effect, and sensitivity to toxic or allergic reactions. A number of these chemical agents are altered metabolically to undergo elimination. These metabolic intermediates may or may not have primary anesthetic activity and they may add to the toxic complications. Unlike electricity, which effect can be turned on and off virtually instantaneously, chemicals remain within the body until the body is able to eliminate them.

The number of complications secondary to all of these anesthetic chemicals are numerous. However, the general categories of these complications are toxicity in its various forms, allergic reactions, and hyper- or hypo-response to the primary effect of the anesthetic agent. Some of the more profound reactions can lead to death, especially in the area of general anesthetic delivery which has a death rate of approximately 1 per 50,000 to 100,000 general anesthetic procedures.

The primary purpose of anesthesia is the control of pain, with desired secondary effects to control patient apprehension and anxiety. Obviously the more complex and involved cases, such as open heart surgery, lung surgery, and intra-abdominal surgery carry tremendous psychological overtones along with the perception of pain. General anesthesia for pain relief and control of patient apprehension is appropriate.

Numerous other less intense surgical procedures are amenable to regional and local anesthetic control allowing the patient to remain conscious during the procedure. Numerous examples range from cranial burr holes for stimulation of the cerebral cortex in mapping procedures to facial surgery, arm and hand surgery, breast biopsies, abdominal hernia surgery, prostate and urinary bladder surgery, leg and foot surgery. In all of the above procedures, prospective pain control is in the form of gas or liquid chemical agents introduced into the patient's body.

A number of procedures are carried out in urgent to emergent circumstances where there in no time to provide adequate prospective pain control. A specific example is the administration of automatic cardioversion/defibrillation shock therapy via an implanted device. These units are designed to respond to cardiac fibrillation or tachycardia and convert the dysrhythmia before the patient suffers any ill effects from the dysrhythmia. The electrical shock therapy delivered to the heart is of high voltage and moderate current causing considerable pain to the patient when it is delivered. No means exist to prospectively block this pain. The perception of pain in patients undergoing cardioversion/defibrillation is mediated through the vagi nerves innervating the heart and peripheral nerves within the chest wall. The pain signals traverse the vagi nerves directly to the brain stem and into the thalamic region of the midbrain. Pain stimulation through the thoracic chest wall peripheral nerves traverses these nerves back to the dorsal root sensory ganglia and into the spinal cord at each vertebral level where the signal is carried up the spinal cord. From this point the perceived pain stimulus disseminates to the appropriate area of the cerebral cortex corresponding to the area of the body from which the signal was received. In this fashion perception of pain is then brought to the conscious awareness of the patient and associated with that specific area of the body.

Perception of pain via the vagus nerve is of a more diffuse generalized sensation due to the nature of the nervous system in perceiving pain from the major thoracic and abdominal organs. Pain perceived via the vagus nerve is described as a pressure pain sensation within the chest and is diffuse, to the extent that the patient is not certain that it comes from the heart specifically but rather the chest generally, In contrast, perception of pain from stimulation of the chest wall peripheral nerves is specific to the area stimulated, and the patient knows exactly where the pain originates.

Prospective pain relief in the circumstances of anticipated cardioversion/defibrillation counter shock therapy in only available at this time in elective cardioversion/defibrillation procedures. The general practice is to provide an anxiolytic agent, such as those known under the trade names Valium®, Versed®, or Ativan®, and an ultra-short acting general anesthetic agent, for example that known under the trade name Brevitol®, from the barbiturate family.

SUMMARY OF THE INVENTION

Numerous surgical and therapeutic procedures result in the patient experiencing pain in the area of the body undergoing the procedure. The invention discloses systems and methods for providing pain relief in anticipation of any surgical or therapeutic procedure, including cardioversion/defibrillation. Pain relief is preferably accomplished by electromagnetic stimulation of appropriate nerve structures.

This invention disclosed means for positioning appropriate electrodes proximate the nerve structures that innervate the area of receive stimulation from the area where the procedure is carried out. Stimulation of the appropriate nerves achieves a blocking of the transmission of the sensory signal and is perceived as anesthesia.

The invention further discloses means for providing further pain relief by direct cerebral cortical stimulation of the sensory area of the cortex that corresponds to the area of the patient's body undergoing the painful procedure.

The above and other objects and advantages will become more readily apparent when reference is made to the following description taken in conjunction with the accompanying drawings.

DETAILED DESCRIPTION OF THE INVENTION

Cardioversion/defibrillation procedures involve the use of high energy electrical countershock therapy to a patient's ailing heart. An undesired effect of this is to cause considerable pain in and around the area of the patient's chest. Pain relief can be provided by interrupting the perception of pain when appropriate nerve blocking stimulation is used on the nerves supplying sensation to the heart and chest.

Figure 1:
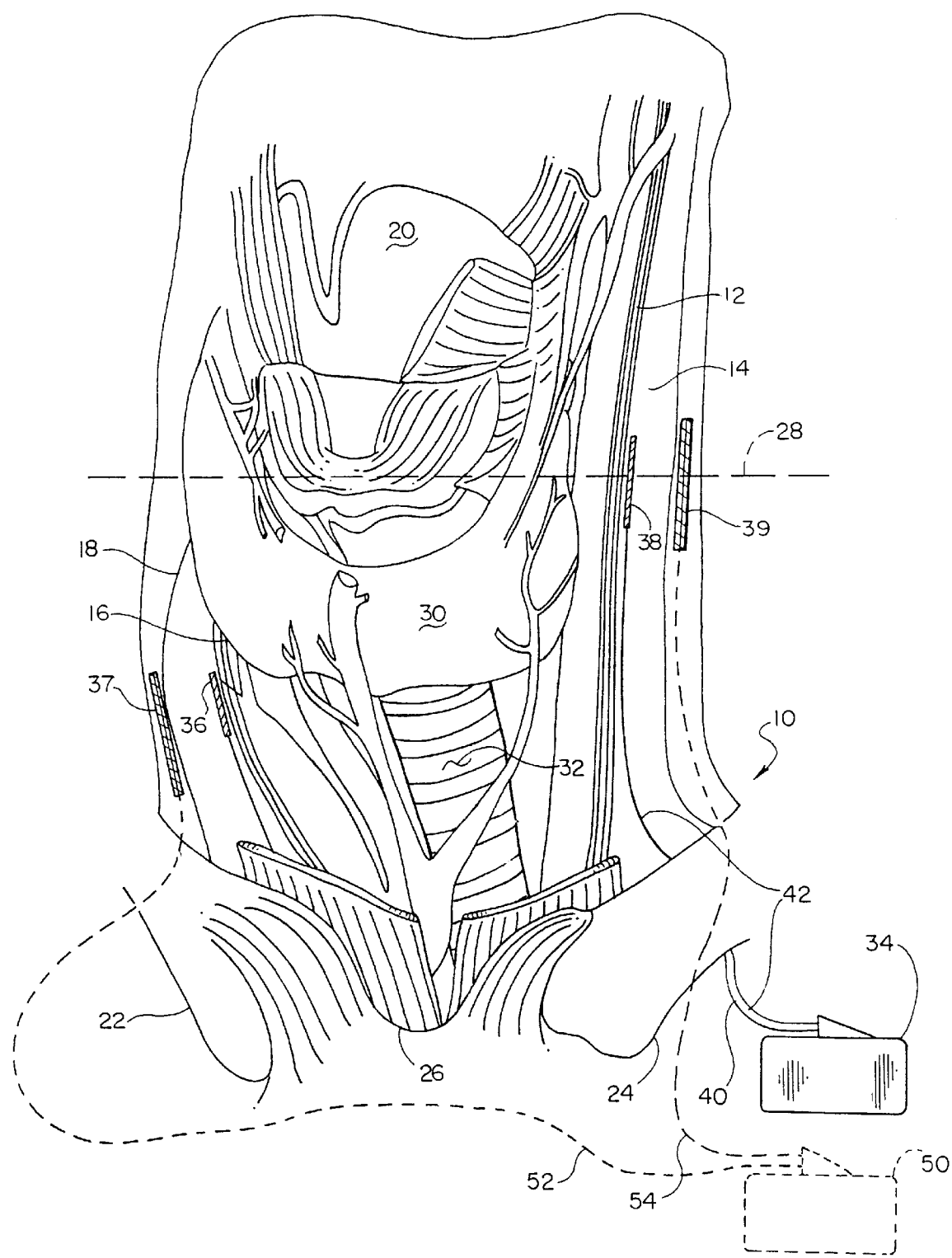
FIG. 1 is a schematic anterior view of the neck with the anterior most skin and musculature removed for clarity of anatomical relationships.

The vagi nerves are primarily autonomic in function, but do supply pain reception fibers to the heart. FIG. 1 discloses a first embodiment of pain control system 10, utilizing vagus nerve stimulation during cardioversion/defibrillation. FIG. 1 is an anterior view of an patient's neck with the anterior skin and musculature removed to view the anatomic relationships of the structures concerned with this invention. The patient's head is slightly turned to the patient's right revealing the close location of the left vagus nerve 12 to the left internal jugular vein 14. A similar proximate relationship also exists with the right vagus nerve 16 and the right internal jugular vein 18. Other landmarks include the thyroid cartilage 20, its prominence correlating with the surface anatomy known as a patient's "Adam's apple". The bottom most aspect of the figure is bordered by the right clavical 22 and left clavical 24 with the sternal notch 26 between these two structures. Sternal notch 26 represents the upper most aspect of the midline anterior chest. The dashed line 28 represents a transverse plane at approximately the fifth cervical vertebral level. Other structures noted in FIG. 1 are the thyroid gland 30 and the trachea 32.

Pain control system 10 of FIG. 1 comprises a pulse generator can 34 which contains power source and control means for providing pain relief stimulation to electrodes, such as electrodes 36, 38. One embodiment anticipates implanting pulse generator can 34 electrically connected to a cardioversion/defibrillation control system, possibly within the same housing, to allow for pain relief stimulation simultaneously with a cardioversion/defibrillation countershock therapy.

Another embodiment would provide for on/off control at a patient's bedside through wireless control means so that a physician, or possibly even the patient, may turn on the pain relief stimulation of system 10 at the bedside prior to a surgical or therapeutic procedure.

Catheters 40 and 42 depicted in FIG. 1 are positioned using an intravascular implantation method. Catheters 40, 42 are passed subcutaneously from pulse generator can 34 into either of the subclavian veins which lay under their respective clavicles, 22, 24. Catheter 40 bearing intravascular electrode 36 is then threaded to a position within the right internal jugular vein 18 such that electrode 36 is proximate right vagus nerve 16. Similar implantation of catheter 42, bearing intravascular electrode 38, brings electrode 38 within left internal jugular vein 18 proximate left vagus nerve 12. Electrodes 36, 38 may lie at various points along the course of an internal jugular vein since right and left vagi nerves 16, 12, respectively, lie closely adjacent to their respective internal jugular veins 18 and 14 through most of the distance within the neck.

Another embodiment of a pain control system is depicted in FIG. 1 by pulse generator can 50, drawn in phantom lines. Pulse generator can 50 is also preferably implanted subcutaneously along with catheters 52 and 54. This alternative method of implantation for a pain control system differs in that catheters 52 and 54 bearing electrodes 37 and 39 respectively have been tunneled through the subcutaneous space from the area fo pulse generator can 50 implantation site to their respective positions with the subcutaneous space of the neck proximate the far lateral aspects of the internal jugular system and vagi nerves. The route of implantation thus carries catheters 52, 54 through the subcutaneous space over right clavical 22 and left clavical 24 as schematically depicted in FIG. 1.

Figure 2:
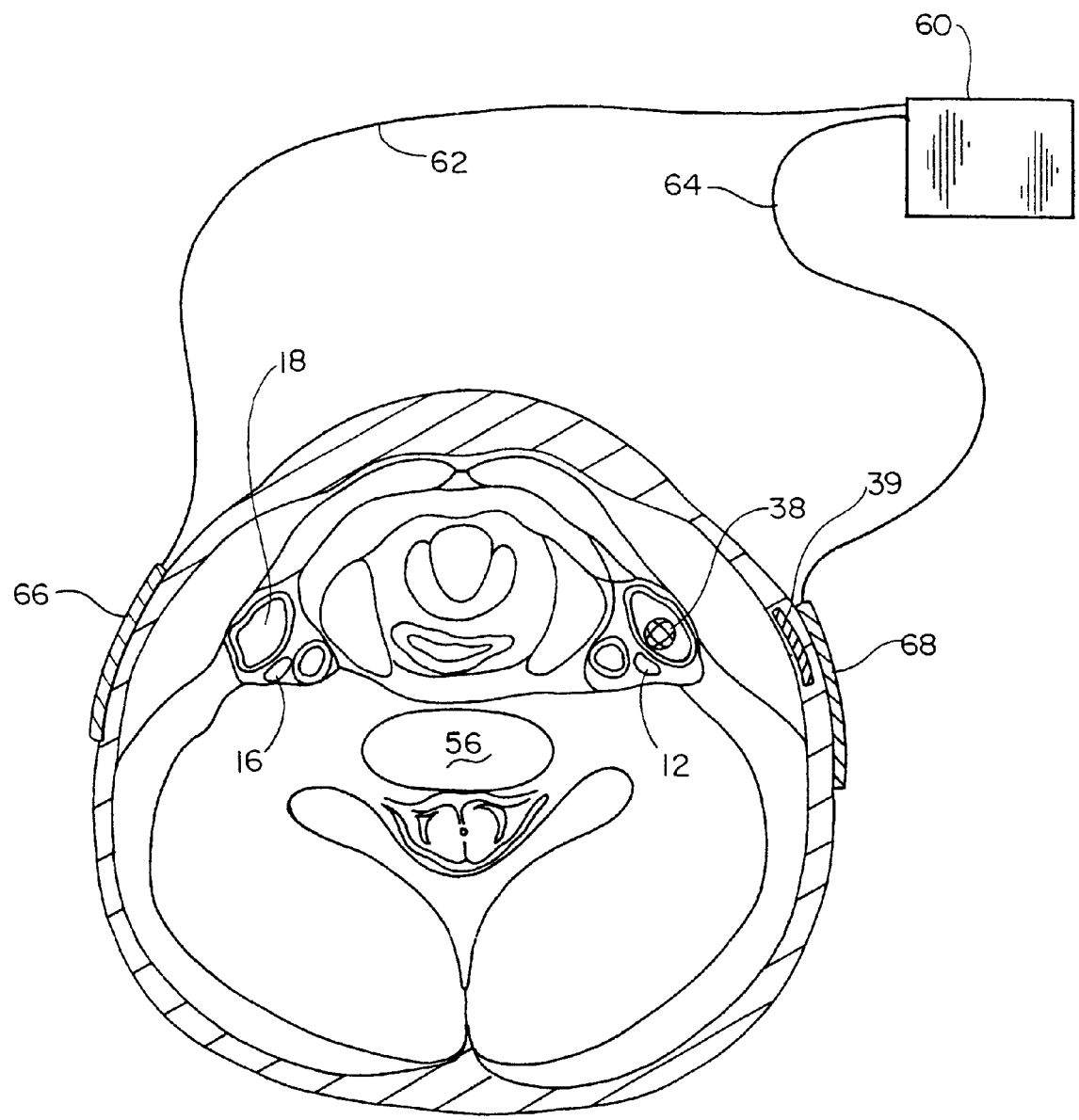
FIG. 2 is a schematic drawing representing the transverse plane of view of the neck at the level depicted in FIG. 1.

FIG. 2 depicts a transverse section view of a patient's neck at approximately the level of the fifth cervical vertebra 56. Proper perspective for FIG. 2 follows traditional anatomic convention so that the viewer is considered to be standing at the patient's feet placing the ventral surface up, the dorsal surface down, the patient's right side corresponds to the left side of FIG. 2, and the patient's left side corresponds to the right side of FIG. 2. As shown in FIG. 2, left jugular vein electrode 38 is proximate left vagus nerve 12. The relative position of subcutaneous electrode 39 is also depicted. Jugular vein electrode 36, in keeping with its positioning in FIG. 1, is not represented in FIG. 2 within right internal jugular vein 18 since it was not placed at transverse level 28.

FIG. 2 depicts a further embodiment of pain control system 10 comprising an external pulse generator can 60 having wires 62 and 64. Pulse generator can 60 provides stimulation to external skin electrodes 66 and 68 placed on the far right lateral and far left lateral aspects of the neck respectively.

The several embodiments of pain control system 10 represented in FIG. 1 and FIG. 2 provide pain reduction stimulation to be applied to the vagi nerves via implanted or external electrode placements. Implanted intravascular electrodes 36, 38 depicted in FIG. 1 allow for long term automatic pain relief stimulation by taking advantage fo circumstances known to cause pain during therapy, such as atrial or ventricular cardioversion/defibrillation countershocks. Similar advantages are foreseen utilizing cutaneous or subcutaneously placed patches where long term prospective pain relief stimulation is anticipated but where the intravascular approach is not used. External patch placement anticipates more urgent and temporary utilization of a pain relief stimulation system which can be synchronized manually in anticipation of performing a painful procedure on the patient. It is recognized that the number and location of electrodes, patches, or other means of stimulation placement depends on a particular patient's requirements.

Figure 3:
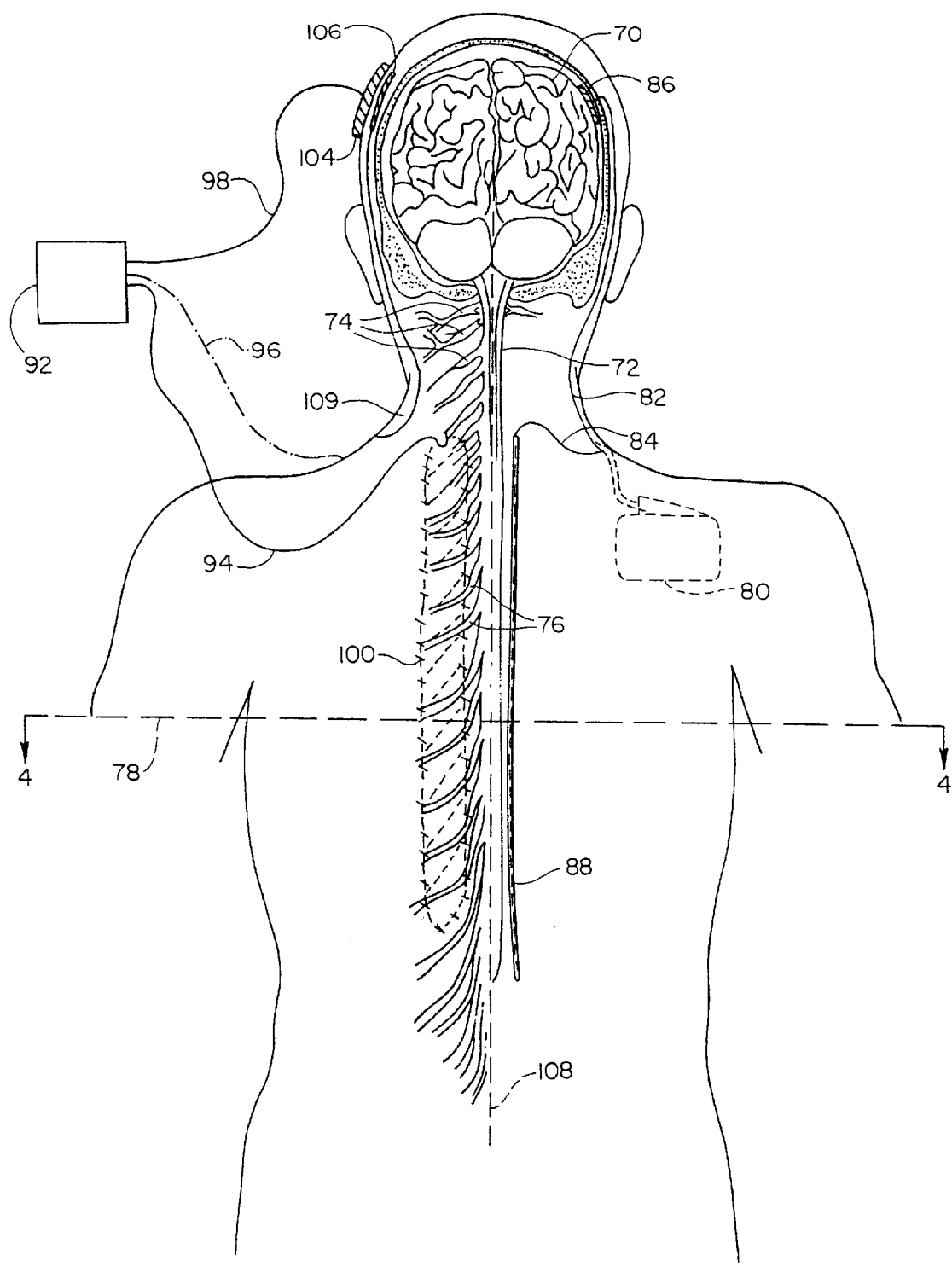
FIG. 3 is a schematic drawing representing the posterior anatomy of a patient depicting the anatomic relationship fo the central nervous system.

Perception of pain within the thorax is primarily mediated through the peripheral sensory nerves found at each vertebral level. FIG. 3 represents a posterior view of a patient showing the relationship of the brain 70, spinal cord 72, and the dorsal sensory ganglia more particularly disclosed at locations 74 and 76. For simplicity and ease of viewing, the dorsal sensory ganglia and peripheral nerves are depicted only on the patient's left side. A representative transverse section view taken along line 78 of FIG. 3 is disclosed in FIG. 4.

In FIG. 3, further alternate embodiments of pain control systems are disclosed. Pulse generator can 80, shown in phantom lines, over the patient's right upper chest area is placed within the subcutaneous space of the patient's chest wall. In this embodiment, two catheters 82 and 84 are connected to pulse generator can 80 and likewise implanted within the subcutaneous space over the scalp and extends through a burr hole in the right frontoparietal skull delivering electrode 86 to the cortex surface of brain 70. In this way electrode 86 can be placed directly over that area of the sensory strip corresponding to the desired area of the patient's body to be anesthetized. The higher up the body requiring pain control, the higher up the surface of brain 70 electrode 86 would likely to be placed. It is anticipated that stimulation of the entire sensory cortex bilaterally could lead to complete body anesthesia. without necessitating a general anesthetic effect and unconsciousness.

Figure 4:
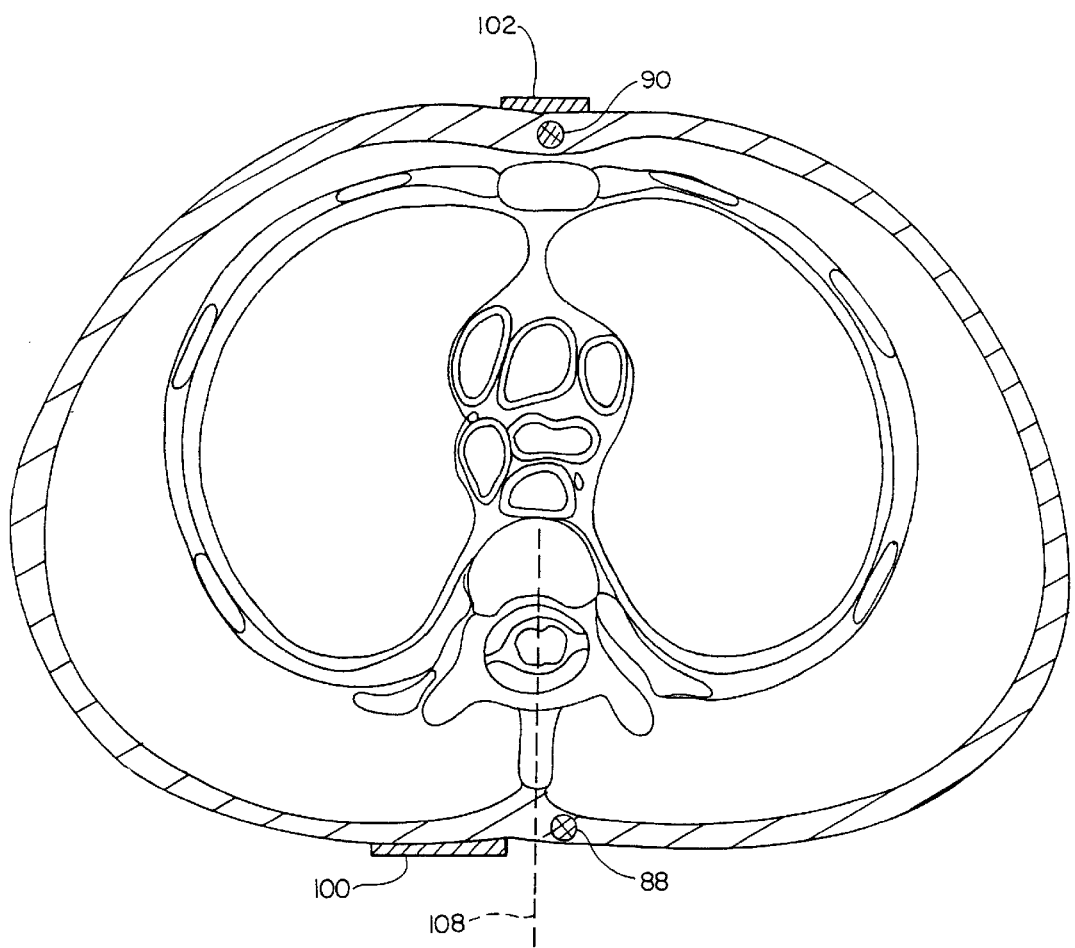
FIG. 4 is a schematic drawing representing a transverse plane of view of the thorax at the level depicted in FIG. 3.

Catheter 84 is depicted as tunneled through the subcutaneous space onto the patient's back, and electrically connected to electrode 88. Electrode 88 parallels the long axis of the thoracic spine and overlays the area where dorsal root sensory ganglia 76 exit spinal cord 72. FIG. 4 discloses electrode 90 placed within the anterior subcutaneous space running parallel to electrode 88 completing the stimulation circuit for pain control to the thoracic dorsal root sensory ganglia.

FIG. 3 discloses a further alternate embodiment of pain control system 10 comprising a pulse generator can 92 connected to appropriate electrodes via wire leads 94, 96, and 98. Wire lead 94 comprises external cutaneous patch electrode 100 which is lying parallel the axis of the spine posteriorly, placing it proximate to the dorsal root sensory ganglia. In FIG. 4, the circuit is completed by a surface skin electrode 102 placed anterior to the chest but is not depicted in FIG. 3 for purposes of clarity. The presence of an anterior chest wall skin patch electrode is alluded to by the presence of wire lead 96 in FIG. 3. Use of a cutaneous patch electrode 100 in this embodiment also anticipates utilization of patch electrodes to either the left or right side of the mid-line 108 enhance pain relief from one side or the other. Alternatively, two electrodes in the posterior position in a bilateral configuration to either side of mid-line 108 would provide stimulation to right and left dorsal root sensory ganglia. Such a configuration in conjunction with anterior surface patch electrode 102 in FIG. 4 provides an electro-magnetic field traversing the bilateral dorsal root sensory ganglia. A similar arrangement is envisioned for the subcutaneously placed electrode 88 and electrode 90. Wire lead 98 in FIG. 3 connects to a scalp skin patch electrode 104 overlaying the sensory strip area of the cerebral cortex. Depending upon the height at which skin patch electrode 104 is placed determines which area of the body is to be rendered anesthetic.

An advantage of this externally applied system embodiment is to provide flexibility in obtaining pain relief in anticipation of various surgical and therapeutic procedures. Utilizing these surface skin electrodes in conjunction with the surface skin electrodes from FIGS. 1 and 2 for placement over the vagi nerves, the pain relief system enables pain blockade for a large portion fo the patient's sensory perception apparatus.

FIG. 3 also discloses a subcutaneous cerebral cortex electrode 106 positioned by catheter 109, which may derive from any of the cans depicted. This arrangement is similar to placement of catheters 82, 84 by tunneling through the subcutaneous space beginning with pulse generator can 80 and ending over the appropriate level of the sensory cerbral cortex. Electrodes 86, 104, and 106 in FIG. 3 are depicted in unilateral positions for purposes of clarity. This invention anticipates the placement of an appropriately configured plurality of electrodes, such as bilateral cerebral cortex electrodes, so that a skin surface patch electrode on the other side and a similar arrangement for cerebral cortex surface electrode 86.

Figure 5:
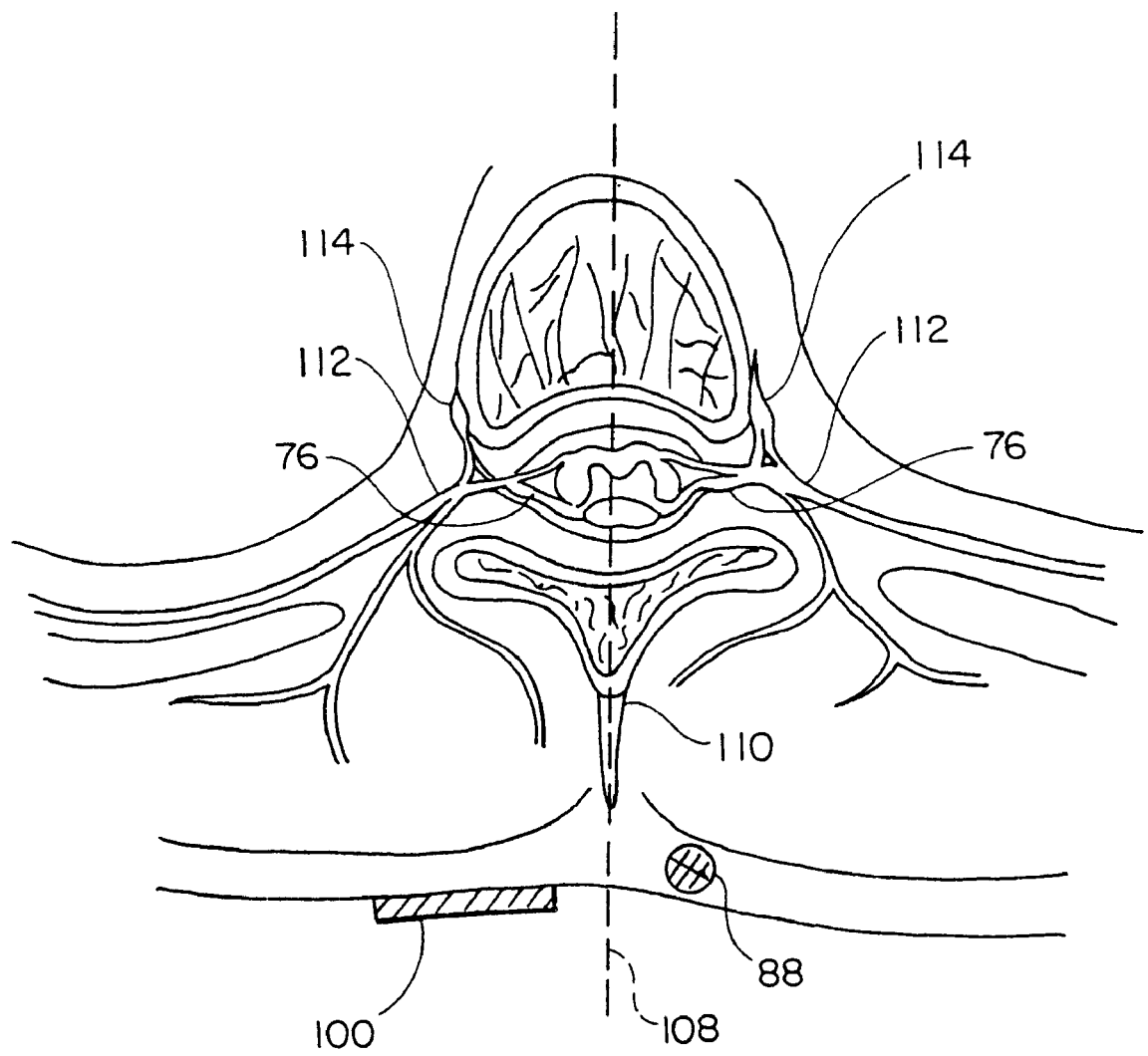
FIG. 5 is a schematic drawing representing a magnified view of the anatomical relationship of nerve bundles at the same level as FIG. 4 as a representation of the nervous system at all levels of the thorax.

FIG. 5 is an enlargement of the posterior spinous structures to further clarify the relative positions of subcutaneous and surface patch electrodes 88 and 100 respectively in relation to the dorsal root sensory ganglia 76. As depicted in FIG. 5, the posterior spinous process element 110 is a bony midline structure with the peripheral nerve roots exiting lateral to this at locations 112 corresponding to the points where sympathetic ganglia 114 pass their afferent and efferent fibers to the peripheral nerve root. Although not depicted, it is envisioned that subcutaneous electrode 88 or cutaneous patch electrode 100 may have bilateral positioning so that there may be right and left subcutaneous electrodes or right and left cutaneous patch electrodes to provide an adequate electromagnetic field through the right and left dorsal root sensory ganglia 76.

The present invention discloses a method and system for providing pain relief during painful procedures in general. A more specific application is for pain relief during defibrillation countershock therapy for cardiac dysrhythmia.

What is claimed is:

1. An improved implantable cardioverter defibrillator system, the implantable cardioverter defibrillator system being a self-contained implantable device for implant within a human patient's body including a pulse-generating capacitor system that stores a high voltage electrical charge, a battery system that internally charges the pulse-generating capacitor system, and a control system that detect cardiac arrhythmias and, in response, selectively discharges the high voltage electrical charge in the pulse-generating capacitor system through therapy-delivery electrodes for implant within the patient's body, the improvement comprising:

a pain-blocking electrode subsystem for implant within the patient's body proximate the vagi nerves and operably connected to the implantable device; and a pain-blocking electrical stimulation system within the implantable device that is electrically connected to the pain-blocking electrode subsystem and the control system and that provides electromagnetic pain nerve blocking stimulation to the pain-blocking electrode subsystem in response to detection of a cardiac arrhythmia and prior to discharge of a high voltage electrical charge.

2. The system of claim 1 wherein the pain blocking electrode subsystem includes at least one implantable pain-blocking electrode selected from the set consisting of a transvenous electrode, a subcutaneous electrode, or any combination thereof.

3. The system of claim 1 wherein the cardiac arrhythmia which triggers the pain-blocking electrical stimulation system is selected from the set consisting of ventricular fibrillation, ventricular tachycardia, atrial fibrillation or atrial tachycardia.

4. An improved implantable cardioverter defibrillator system, the implantable cardioverter defibrillator system being a self-contained implantable device for implant within a human patient's body including a pulse-generating capacitor system that stores a high voltage electrical charge, a battery system that internally charges the pulse-generating capacitor system, and an control system that detects cardiac arrhythmmias and, in response, selectively discharges the high voltage electrical charge in the pulse-generating capacitor system through therapy-delivery electrodes for implant within the patient's body, the improvement comprising:

a pain-blocking electrode subsystem for implant within the patient's body proximate the thoracic dorsal spinal nerves and operably connected to the implantable device; and a pain-blocking electrical stimulation system within the implantable device that is electrically connected to the pain-blocking electrode subsystem and the control system and that provides electromagnetic pain nerve blocking stimulation to the pain-blocking electrode subsystem in response to detection of a cardiac arrhythmia and prior to discharge of a high voltage electrical charge.

5. The system of claim 4 wherein the pain blocking electrode subsystem includes at least one implantable pain-blocking electrode selected from the set consisting of a transvenous electrode, a subcutaneous electrode, or any combination thereof.

6. The system of claim 4 wherein the cardiac arrhythmia which triggers the pain-blocking electrical stimulation system is selected form the set consisting of ventricular fibrillation, ventricular tachycardia, atrial fibrillation or atrial tachycardia.

7. An improved implantable cardioverter defibrillator system, the implantable cardioverter defibrillator system being a self-contained implantable device for implant within a human patient's body including a pulse-generating capacitor system that stores a high voltage electrical charge, a battery system that internally charges the pulse-generating capacitor system, and a control system that detects cardiac arrhythmias and, in response, selectively discharges the high voltage electrical charge in the pulse-generating capacitor system through therapy-delivery electrodes for implant within the patient's body, the improvement comprising:

a pain-blocking electrode subsystem comprising a plurality of electrodes mounted along a transvenous lead for implant within the venous vasculature of the patient's body and operably connected to the implantable device; and a pain-blocking electrical stimulation system within the implantable device that is electrically connected to the pain-blocking electrode subsystem and the control system and that provides electromagnetic pain nerve blocking stimulation to the pain-blocking electrode subsystem in response to detection of a cardiac arrhythmia and prior to discharge of a high voltage electrical charge.

8. The system of claim 7 wherein the cardiac arrhythmia which triggers the pain-blocking electrical stimulation system is selected from the set consisting of ventricular fibrillation, ventricular tachycardia, atrial fibrillation or atrial tachycardia.

* * * * *